United States Patent [19]

Schonfeld et al.

[11] Patent Number: 4,646,730

[45] Date of Patent: Mar. 3, 1987

[54] COLOR STABILIZED HYDROGEL DRESSING AND PROCESS

[75] Inventors: Edward Schonfeld, New York, N.Y.; James W. McGinity, Austin, Tex.

[73] Assignee: Johnson & Johnson Products, Inc., New Brunswick, N.J.

[21] Appl. No.: 866,541

[22] Filed: May 23, 1986

[51] Int. Cl.$^4$ .............................................. A61L 15/00
[52] U.S. Cl. ..................................... 728/156; 604/368
[58] Field of Search ....................... 128/156, 159, 289; 604/368; 427/449

[56] References Cited

U.S. PATENT DOCUMENTS

| | | | |
|---|---|---|---|
| 4,192,727 | 3/1980 | Ward | 128/156 |
| 4,209,605 | 6/1980 | Hoy | 128/156 |
| 4,263,185 | 4/1981 | Belykh | 128/156 |
| 4,362,841 | 12/1982 | Minatono | 128/156 |
| 4,377,010 | 3/1983 | Fydelor | 128/156 |
| 4,411,754 | 10/1983 | Kaotsu | 128/156 |
| 4,548,847 | 10/1985 | Aberson | 128/156 |
| 4,552,138 | 11/1985 | Hofoditz | 128/156 |

*Primary Examiner*—Gregory E. McNeill

[57] ABSTRACT

A polyvinylpyrrolidone(PVP)/Silver Sulfadiazine (SSD) hydrogel dressing in which the gel is formed by the use of electron beam (E-Beam) radiation to crosslink the polyvinylpyrrolidone (PVP); in which the color of the hydrogel dressing has been stabilized by the addition thereto of magnesium trisilicate and, optionally but preferably, also hydrogen peroxide and/or polyacrylic acid is disclosed; and also the process of stabilizing the color by adding magnesium trisilicate, to a water dispersion of PVP and SSD before it is exposed to E-Beam radiation is disclosed.

10 Claims, No Drawings

COLOR STABILIZED HYDROGEL DRESSING AND PROCESS

This invention relates to a Polyvinylpyrrolidone (PVP)/Silver Sulfadiazine (SSD) hydrogel dressing in which the gel is formed by the use of electron beam (E-Beam) radiation to cross-link the polyvinylpyrrolidone (PVP); and is more particularly concerned with such a gel dressing in which the color of the hydrogel dressing has been stabilized by the addition thereto of magnesium trisilicate and, optionally but preferably, also hydrogen peroxide and/or polyacrylic acid; and to the process of stabilizing the color by adding magnesium trisilicate, and optionally hydrogen peroxide and/or polyacrylic acid, to a water dispersion of PVP and SSD before it is exposed to E-beam radiation.

BACKGROUND OF THE INVENTION

Various medicated and unmedicated hydrogel dressings containing polyvinylpyrrolidone (PVP) are known.

Johnson & Johnson manufactures "Therapeutic Gel Dressing", which is a clear, semi-firm, cross-linked PVP/water gel, supported by an internal nonwoven web and a polyethylene backing, whose active surface is protected by a removable polyethylene release film. It is packaged in a shallow tray inside a foil peel-open pouch.

EPO Patent Application No. 83305770.6, published May 2, 1984, discloses a hydrogel absorbent wound dressing comprising a non-rigid layer of cross-linked polyvinylpyrrolidone (PVP) gel. The gel is preferably prepared by dissolving 15-25 percent by weight of PVP in water and cross-linking the PVP by means of ionizing radiation. A radiation level of between 1-5 MRADS, preferably from an electron beam, is used to effect cross-linking.

Said EPO patent application (a) teaches that it is desirable to add various medicaments to such a dressing, one preferred medicament being silver sulfadiazine (SSD) which is well known as an effective antibacterial agent, and (b) discloses a PVP gel dressing incorporating SSD.

When repeating the above-disclosed process, after the water dispersion of PVP/SSD was exposed to electron beam (E-Beam) radiation to form the gel, it was found that the color of the resulting medicated hydrogel dressings containing PVP/silver sulfadiazine (PVP/SSD) is an assortment of various colors (e.g. yellow, purple, green, brown, etc.). The shades of color in the gel change with aging, but remain different and mottled. This color problem is severe since E-Beam radiation is a necessary part of a preferred process of preparing the gel dressings, in which radiation is used to cross-link the PVP matrix and to transform the flowable dispersion of PVP/SSD into an insoluble, non-flowable gel. The variability of color of such a hydrogel wound dressing is not acceptable in medical applications since a medical practitioner would doubt the reliability of a non-standard, changeable product. The mottled product of many different colors, and shades of colors, while perfectly suitable from a utilitarian point of view, is esthetically unpleasing and completely contrary to what is considered acceptable in medical practice. Alternate methods, therefore, were sought to stabilize the color of the PVP/SSD gel in order to obtain a gel of uniform color.

SUMMARY OF THE INVENTION

It was unexpectedly found that the addition of magnesium trisilicate to the starting PVP/SSD aqueous dispersion results in a hydrogel product which had a uniform deep yellow color after undergoing E-Beam radiation. This color remained even after extended aging at 120° F., showing it would be expected to retain this color over a long shelf life.

A further improvement was unexpectedly found when polyacrylic acid was added to the dispersion of PVP/SSD/magnesium trisilicate/water. After exposure to E-Beam radiation, a gelled product was obtained which had a significant lighter, uniform yellow color than without the polyacrylic acid both initially and after extended aging at 120° F.

It was further unexpectedly found that the addition of hydrogen peroxide to the dispersion of PVP/SSD/magnesium trisilicate/water before exposure to E-Beam radiation resulted in a gel having a uniform milk-white color.

It is known in the prior art to incorporate glycerine (glycerol; 1,2,3-propane triol) into a PVP hydrogel. One effect of this is to improve tackiness, which can be an advantage in a hydrogel wound dressing. Using glycerine, it is possible to use lesser radiation levels of E-beam radiation, e.g. 0.5 MRADS, and still obtain a PVP hydrogel with good tackiness and other desired properties. [In such a case, it is possible, if desired, to use cobalt radiation to sterilize the PVP hydrogel which was made using E-beam radiation.] It would be desirable to incorporate SSD in such wound dressings also. However, it was found that PVP hydrogels containing both glycerine and SSD exhibit the same kind of color problems as those without glycerine when exposed to E-Beam radiation. The color of such gels is an assortment of various colors, such as yellow, purple, green, and brown, etc., which is equally unacceptable here as in the non-glycerine containing gel.

Fortunately, the same general methods of color stabilization as described above were unexpectedly found also to work with the glycerine containing PVP/SSD gels. The glycerine/PVP/SSD/magnesium trisilicate gel dressing of the present invention was found to have a uniform yellow color, which color is a somewhat darker shade of yellow than corresponding gels prepared without glycerine. The addition of polyacrylic acid to such a gel reduced the dark yellow color associated with the gels containing glycerine to a lighter yellow. The addition of hydrogen peroxide to the dispersion of glycerine/PVP/SSD/magnesium trisilicate/water resulted in a gel having a uniform milk-white color, after exposure to E-beam radiation.

The present invention includes all aspects of the color stabilization process disclosed herein and all variants of the resultant color stabilized PVP/SSD hydrogel dressings, i.e., whether or not glycerine is used in the PVP/SSD hydrogel dressing, and whether the magnesium trisilicate is used alone, or together with polyacrylic acid and/or hydrogen peroxide as the color stabilizing agent(s). Without intending to be bound thereby, it is thought the metallic oxides (MgO and $SiO_2$) normally found with magnesium trisilicate react with residual peroxides which are present in PVP resin, changing such peroxides which are known color formers, into the more stable metallic peroxides. It is further thought that polyacrylic acid chelates with the soluble Ag ion portion of SSD, not allowing the highenergy electrons of the radiation to turn the Ag ion into a dark yellow color. It also is thought that hydrogen peroxide acts to bleach the color. However, even though hydrogen peroxide is a known bleaching agent, its use in the instant invention is unexpected in that other bleaching agents tried did not work, and also in that the use of hydrogen peroxide without the magnesium trisilicate was ineffective to stabilize the various colors otherwise obtained after exposure to E-Beam radiation.

DETAILED DESCRIPTION OF THE INVENTION

For purposes of this invention, any form of the cross-linked PVP/SSD dressings referred to above can be utilized, and the exact amounts of PVP and SSD (and optionally glycerine) used in the process of manufacture are not critical. It is contemplated that generally the same process, procedures and amounts of materials should be used to make the gel as if the color of the gel did not matter.

The magnesium trisilicate should be present in an amount sufficient to provide color stabilization, i.e., a color stabilizing amount. The concentration of magnesium trisilicate effective for color stabilization for use in the present invention is 0.5 percent or above. The amount normally used should be between about 0.5 and 5.0 percent of the total weight of the gel, preferably between 0.5 and 2.0 percent and most preferably one percent.

The concentration of polyacrylic acid necessary for color reduction for use in the present invention has been determined to be between about 0.05 and 0.7 percent of the total weight of the gel, and preferably 0.2 percent.

While we have heretofore disclosed and discussed the use of polyacrylic acid in connection with present invention, it has also been found that the use of polymethacrylic acid in place of polyacrylic acid is also effective, but to a lesser extent, in reducing the color of PVP/SSD/magnesium trisilicate gels. Furthermore, it is also possible to use acrylic acid monomer in place of polyacrylic acid. This monomer can be polymerized in situ by E-Beam radiation, and is also effective in promoting the color reduction of PVP/SSD/magnesium trisilicate gels. However, in order to avoid the possibility of any unreacted acrylic acid monomer remaining in the final gel which will be used as a wound dressing, the use of preformed polyacrylic acid is preferred.

The amount of hydrogen peroxide ($H_2O_2$) effective for color reduction is 0.25 or above. The amount normally used should be between about 0.25 and 1.0 percent of the total weight of the gel, preferably between 0.25 and 0.50, with the optimum being 0.25 percent. 0.125 percent was not effective in preventing the formation of the yellow color upon heat aging.

While we prefer to utilize already polymerized PVP as the starting material, it is known to utilize vinyl pyrrolidone (VP) monomer as the starting material which is then polymerized by the E-Beam radiation. We regard this as the full equivalent of our process for purposes of this invention. In order to avoid the possibility of leaving unreacted VP monomer in the gel, however, the use of the preformed PVP is preferred.

The following are actual working examples. They will serve to illustrate various preferred forms of the present invention, which is not to be regarded as limited thereto. All parts or percentages shown in the examples are by weight. The various amounts of ingredients shown are in grams (g) unless otherwise specified.

EXAMPLE I

Control Gel with No Additives

The ingredients used are:
PVP (K-90, GAF): 200 g
Deionized Water: 795 g
Silver Sulfadiazine: 5 g Mix the PVP and SSD and add the resultant powder slowly to the water using good agitation with a turbine stirrer. Mix for 30 minutes, after addition of the PVP, until the solution is a uniform, viscous mass.

[If desired, optionally deaerate the solution, e.g., by putting it in a pail, heating slowly to 100° F. until the bubbles rise to the surface and break. This was not done in carrying out the example in the laboratory, but should be done for scale-up repetitions.] Then cast it onto a polyethylene film. Cover with a nonwoven web and then with a second polyethylene film and press to the desired thickness (0.040"). Diecut to a 4"×4" square, place in an aluminum pouch, and heat seal. The sealed pouch is then exposed to 3.0 megarads of electron beam radiation (800 KV, 3.0 milliamps at a line speed of 10 ft/min) to gel the solution.

Samples were placed in 120° F. aging room for two weeks. Each of the gels had an assortment of mottled dark colors in the yellow, green, brown range. These were unacceptable in not appearing to look pure or uniform.

EXAMPLE II

Addition of Magnesium Trisilicate

Ingredients used were:
PVP (K-90, GAF): 200 g
Deionized Water: 785 g
Silver Sulfadiazine: 5 g
Magnesium Trisilicate: 10 g The PVP, SSD and magnesium trisilicate were mixed together. The same procedure was thereafter followed as with the control of Example I.

The resultant gel samples were a uniform deep yellow color after two weeks of aging at 120° F. These are considered acceptable in appearance.

EXAMPLE III

Addition of Polyacrylic Acid and Magnesium Trisilicate

The ingredients used were:
PVP (K-90, GAF): 200 g
Deionized Water: 783 g
Silver Sulfadiazine: 5 g
Mg. Trisilicate: 10 g
Polyacrylic Acid: 2 g The polyacrylic acid was dissolved in a little water, and added to the PVP, SSD and magnesium trisilicate, and blended together. Thereafter, the same procedure was followed as with the preceding Examples I and II.

The resultant gel samples were a uniform pale yellow color after two weeks of aging at 120° F.

EXAMPLES IV–VII

Addition of Glycerine

The ingredients used are as shown below. The procedures used are as in the preceding Examples I and II. Where glycerine is used, it is admixed with the water.

The appearance of the resultant gel samples, after aging is as shown below.

| Example No. | IV | V | VI | VII |
| --- | --- | --- | --- | --- |
| PVP | 200 | 200 | 200 | 200 |
| H₂O | 785 | 735 | 783 | 733 |
| Glycerine | — | 50 | — | 50 |
| SSD | 5 | 5 | 5 | 5 |
| Mg. Trisilicate | 10 | 10 | 10 | 10 |
| Polyacrylic Acid | — | — | 2 | 2 |
| 2 wks at 120° F. | Yellow | Dark Yellow | Very Pale Yellow | Pale Yellow |

EXAMPLES VIII–X

Addition of Hydrogen Peroxide

The ingredients used are as shown below for Example VIII. The procedures used are as in the preceding Examples I and II. In Examples IX and X, the dispersion of Example VIII is used, and the amount of hydrogen peroxide shown is added to the amounts of dispersion shown. The hydrogen peroxide was in the form of a 30 percent solution in water (J. B. Baker "Superoxol").

| Example No. | VIII | IX | X |
| --- | --- | --- | --- |
| PVP | 200 | | |
| H₂O | 783 | 99.17 | 99.59 |
| Mg. Trisilicate | 10 | | |
| SSD | 5 | | |
| Polyacrylic acid | 2 | | |
| H₂O₂-(30%) | — | 0.83 | 0.41 |

The appearance of the resultant gel samples is as shown in Table I, after the Examples. These three examples show the effect of hydrogen peroxide, in varying amounts.

EXAMPLES XI–XII

Addition of Hydrogen Peroxide (without Mg Trisilicate)

The ingredients used are as shown below, and the procedures used are as in Examples I and II. In Example XII, the dispersion of Example XI is used in the amount shown, to which is added the amount of polyacrylic acid shown.

| Example No. | XI | XII |
| --- | --- | --- |
| PVP | 200 | |
| H₂O | 786.7 | |
| SSD | 5 | 99.8 |
| Polyacrylic Acid | — | 0.2 |
| H₂O₂-(30%) | 8.3 | |

The appearance of the resultant gel samples is as shown in Table I. From Examples X, XI and XII, it can be seen that Magnesium Trisilicate must be present also for the Hydrogen Peroxide to be effective.

EXAMPLES XIII AND XIV

H₂O₂ with and without PAA

The ingredient used are as shown below, with the dispersion of Example XIII being used in Example XIV together with the polyacrylic acid (PAA) in the amount shown. The gels were made by the procedures of Examples I and II.

| Example No. | XIII | XIV |
| --- | --- | --- |
| PVP | 200 | |
| H₂O | 776.6 | |
| Mg. Trisilicate | 10 | 99.8 |
| SSD | 5 | |
| Polyacrylic Acid | — | 0.2 |
| H₂O₂-(30%) | 8.4 | |

The appearance of the resultant gels, shown in Table I, indicates that it is not necessary to have PAA present, where magnesium trisilicate and H₂O₂ are both used, for color stabilization.

TABLE I

The following is a comparison of the color of the hydrogels of Examples VIII–XIV, initially and after accelerated aging at 120° F. for 1, 2, and 3 weeks.

| Ex No. | Initial Color | Heat Aging @ 120° F. | | |
| --- | --- | --- | --- | --- |
| | | 1 Wk. | 2 Wks | 3 Wks |
| VIII | Cream | yellow | yellow | yellow |
| IX | white | white | white | white |
| X | off-white | cream | light yellow | light yellow |
| XI | white | cream | light yellow | yellow |
| XII | white | cream | light yellow | light yellow |
| XIII | white | white | white | off-white |
| XIV | white | white | white | off-white |

EXAMPLES XV AND XVI

Addition of H₂O₂ with and without Glycerine

The ingredients used are as shown below. The procedures used are as in Examples I and II. Where glycerine is used is admixed with the water. The appearance of the resulting gel samples, initially and after aging, was a uniform color as shown below.

| Example No. | XV | XVI |
| --- | --- | --- |
| PVP | 200 | 200 |
| H₂O | 774.7 | 774.7 |
| SSD | 5 | 5 |
| Mg. Trisilicate | 10 | 10 |
| Polyacrylic Acid | 2 | 2 |
| H₂O₂-(30%) | — | 8.85 |
| Glycerine | 49.6 | 49.6 |
| Initial Color: | beige/yellow | white |
| 1 week at 120° F. | beige/yellow | white |

EXAMPLE XVII (A)–(F)

Use of Varying Amounts of E-Beam Radiation Followed by Cobalt Radiation Sterilization Following the procedures used in Examples I and II, the ingredients shown below were used, in seven comparative examples (A)–(F), which used identical procedures, except that the amount of E-beam radiation (EB dose) was as shown below. The resultant hydrogel samples were then sterilized using cobalt radiation (cobalt dose). The color of each sample, initially and after aging, was as specified, the colors being uniform throughout the sample. As shown below, the cross-linked PVP gels differed in how tacky their surfaces were, with the amount of tackiness decreasing inversely with the E-beam dose used.

| Example No. | | XVII | | |
|---|---|---|---|---|
| PVP | | 200 g | | |
| H₂O | | 783 g | | |
| SSD | | 5 g | | |
| Mg. Trisilicate | | 10 g | | |
| Polyacrylic Acid | | 2 g | | |

| | | | Color | |
|---|---|---|---|---|
| | EB Dose | Cobalt Dose | Initial | 1 wk @ 120° F. | Tack |
| A | 0.5 MRADS | 2.5 MRADS | white | v/pale yellow | most tack |
| B | 1.0 MRADS | 2.5 MRADS | white | v/pale yellow | |
| C | 1.5 MRADS | 2.5 MRADS | white | v/pale yellow | |
| D | 2.0 MRADS | 2.5 MRADS | white | v/pale yellow | |
| E | 2.5 MRADS | 2.5 MRADS | white | v/pale yellow | |
| F | 3.0 MRADS | 2.5 MRADS | white | v/pale yellow | least tack |

ILLUSTRATION A-EFFECT OF A NON-HYDROGEN PEROXIDE BLEACHING AGENT

This illustration shows that, in contrast to results obtained with hydrogen peroxide as shown in Examples VIII–X, XIII and XIV, the use of another well-known bleaching agent resulted in a dark brown gel, which is not a satisfactory color. This shows the uniqueness of $H_2O_2$.

Following the procedures used for the $H_2O_2$ gels referred to above, with the ingredients shown below, it was found that the use of another oxidizing agent sodium hypochlorite (Chlorox) (in place of $H_2O_2$) turned the sample gels dark brown:

PVP: 200 g
H₂O: 783 g
SSD: 5 g
Mg. Trisilicate: 10 g
Polyacrylic Acid: 2 g
Chlorox (5.25%): 92.8 g

What is claimed is:

1. A color stabilized hydrogel dressing comprising a non-rigid layer of cross-linked polyvinylpyrrolidone gel having incorporated therein at least 0.1 percent by weight of silver sulfadiazine, which gel has been exposed to E-beam radiation, and which gel also contains a color stabilizing amount of magnesium trisilicate.

2. The color stabilized hydrogel dressing of claim 1 wherein the magnesium trisilicate is present in an amount between 0.5 and 5.0 percent, based on the total weight of the gel.

3. The color stabilized hydrogel dressing of claim 2 wherein the magnesium trisilicate is present in an amount between 0.5 and 2.0 percent.

4. The color stabilized hydrogel dressing of claim 1 which also contains glycerine.

5. The hydrogel dressing of claims 1 or 4 which also contains between 0.05 and 0.7 percent of polyacrylic acid or polymethacrylic acid, based on the total weight of the gel.

6. The stabilized hydrogel dressing of claims 1, 4 or 5, which also contains from 0.25 to one percent by weight of hydrogen peroxide.

7. The process of stabilizing the color of the polyvinylpyrrolidone silver sulfadiazine gel dressing which results from the E-Beam radiation of a water dispersion of polyvinylpyrrolidone and silver sulfadiazine which comprises adding magnesium trisilicate to the water dispersion before it is exposed to E-beam radiation.

8. The process of claim 7 wherein polyacrylic acid or polymethacrylic acid or acrylic acid monomer is added to the polyvinylpyrrolidone/silver sulfadiazine/magnesium trisilicate water dispersion before said dispersion is exposed to E-Beam radiation.

9. The process of claim 8 wherein hydrogen peroxide is added to the polyvinylpyrrolidone/silver sulfadiazine/magnesium trisilicate containing water dispersion before said dispersion is exposed to E-Beam radiation.

10. The process of claim 7, 8 or 9 in which glycerine is also added to the polyvinylpyrrolidone silver sulfadiazine/magnesium trisilicate containing water dispersion prior to exposure to E-Beam radiation.

* * * * *